US009220464B2

(12) United States Patent
Terai et al.

(10) Patent No.: US 9,220,464 B2
(45) Date of Patent: Dec. 29, 2015

(54) MEDICAL INFORMATION MANAGEMENT DEVICE

(71) Applicants: KABUSHIKI KAISHA TOSHIBA, Tokyo (JP); Toshiba Medical Systems Corporation, Otawara-shi (JP)

(72) Inventors: Koichi Terai, Otawara (JP); Kenichi Niwa, Otawara (JP); Masato Shibuya, Otawara (JP); Maiko Tezuka, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 126 days.

(21) Appl. No.: 13/850,498

(22) Filed: Mar. 26, 2013

(65) Prior Publication Data

US 2013/0249702 A1 Sep. 26, 2013

(30) Foreign Application Priority Data

Mar. 26, 2012 (JP) ................................. 2012-070047
Feb. 22, 2013 (JP) ................................. 2013-033757

(51) Int. Cl.
*G08B 3/00* (2006.01)
*A61B 5/00* (2006.01)
*G06F 19/00* (2011.01)
*A61B 1/00* (2006.01)
*G06F 1/00* (2006.01)

(52) U.S. Cl.
CPC ............ *A61B 5/743* (2013.01); *G06F 19/3487* (2013.01); *A61B 1/00* (2013.01); *G06F 1/00* (2013.01)

(58) Field of Classification Search
CPC .................................... G06F 1/00; A61B 1/00
USPC ............................................ 340/691.6; 705/3
See application file for complete search history.

(56) References Cited

U.S. PATENT DOCUMENTS

2006/0265253 A1* 11/2006 Rao et al. ........................ 705/3
2010/0088116 A1* 4/2010 Eisenberg et al. ............... 705/3

FOREIGN PATENT DOCUMENTS

| JP | 2003-296444 | 10/2003 |
| JP | 2009-32145 | 2/2009 |
| JP | 2010-262592 | 11/2010 |
| JP | 2012-150704 | 8/2012 |

* cited by examiner

*Primary Examiner* — Shirley Lu
(74) *Attorney, Agent, or Firm* — Oblon, McClelland, Maier & Neustadt, L.L.P.

(57) ABSTRACT

According to one embodiment, a display unit displays a screen of a medical application. An acquisition unit acquires a plurality of values used in the medical application and belonging respectively to a plurality of monitoring items set in advance. A determination unit determines whether the acquired values satisfy a matching determination rule for relevance of presence or absence of a change in a value of a reference item among a plurality of monitoring items in the medical application and presence or absence of a change in a value of the other item. An alerting unit controls the display unit to display an alert when it is determined by the determination unit that the acquired values do not satisfy the matching determination rule.

10 Claims, 7 Drawing Sheets

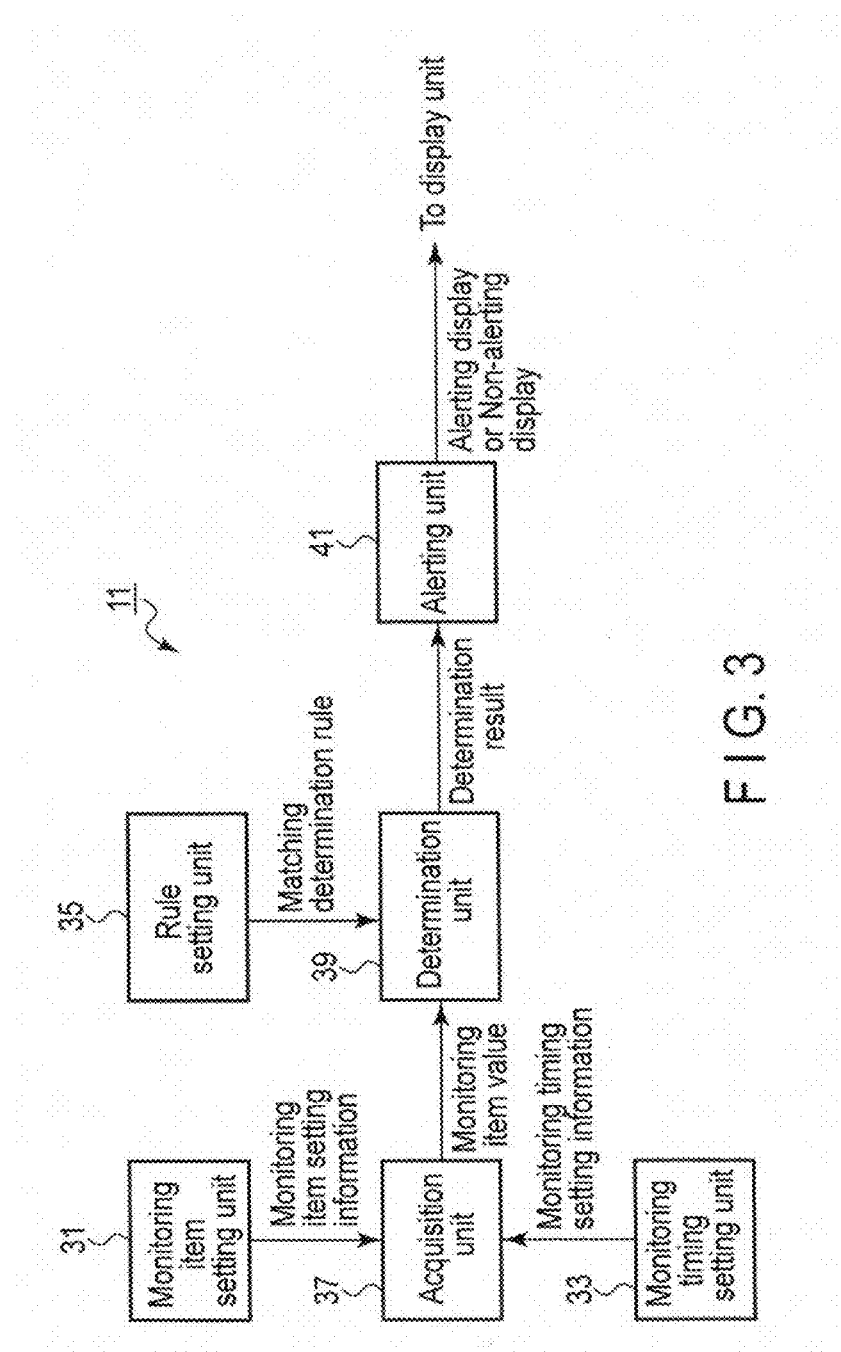
F I G. 3

Patient information
Patient ID: 0001
Name: Toshiba Taro
Date of birth: 1997/01/01
Sex: Male

Finding
Ascites is recognized around a stomach and an intestinal tract and is slightly increasing

Diagnosis
After middle bile duct cancer surgery. A hole is suspected to be formed in a front inferior vena cava

Past report list

| Examination date | Modality | Part | Age |
|---|---|---|---|
| 2010/02/05 | CT | Abdomen | 13 |
| 2010/02/10 | MR | Head | 13 |
| 2010/02/15 | CT | Abdomen | 13 |

Past report

Patient ID displayed on screen RI

Past report list

| Examination date | Modality | Part | Age |
|---|---|---|---|
| 2010/02/05 | CT | Abdomen | 13 |
| 2010/02/10 | MR | Head | 13 |
| 2010/02/15 | CT | Abdomen | 13 |

Patient information
- Patient ID:0001
- Name: Toshiba Taro
- Date of birth:1997/01/01
- Sex: Male Finding
Ascites is recognized around a stomach and an intestinal tract and is slightly increasing Diagnosis
After middle bile duct cancer surgery. A hole is suspected to be formed in a front inferior vena cava Past report

RI

Patient ID displayed on screen II

Patient information
- Patient ID:0001
- Name: Toshiba Taro
- Date of birth:1997/01/01
- Sex: Male Examination information
- Examination date:2010/02/10
- Examination: MR
- Part: Head Examination image

II

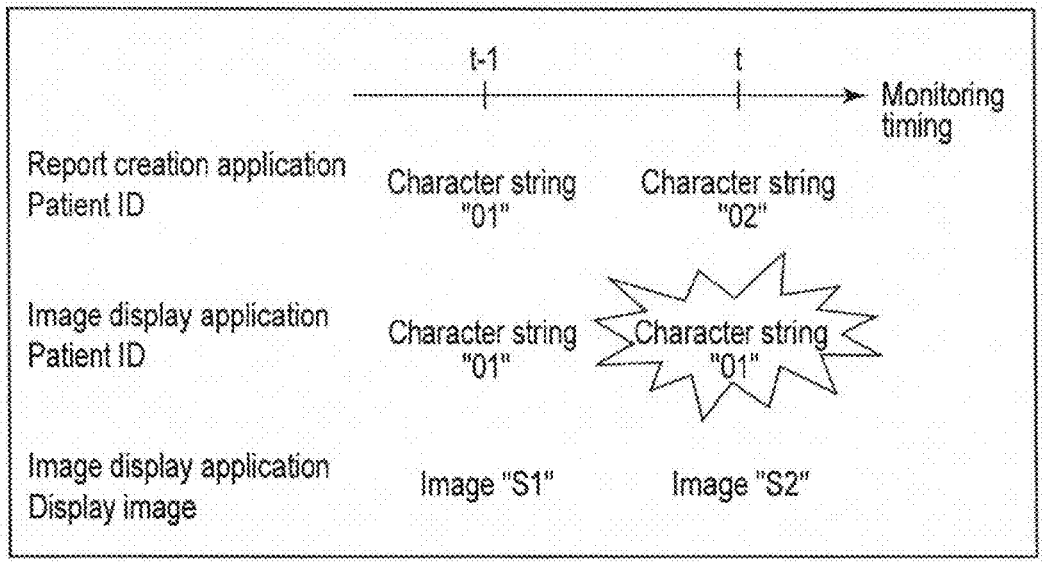
F I G. 6
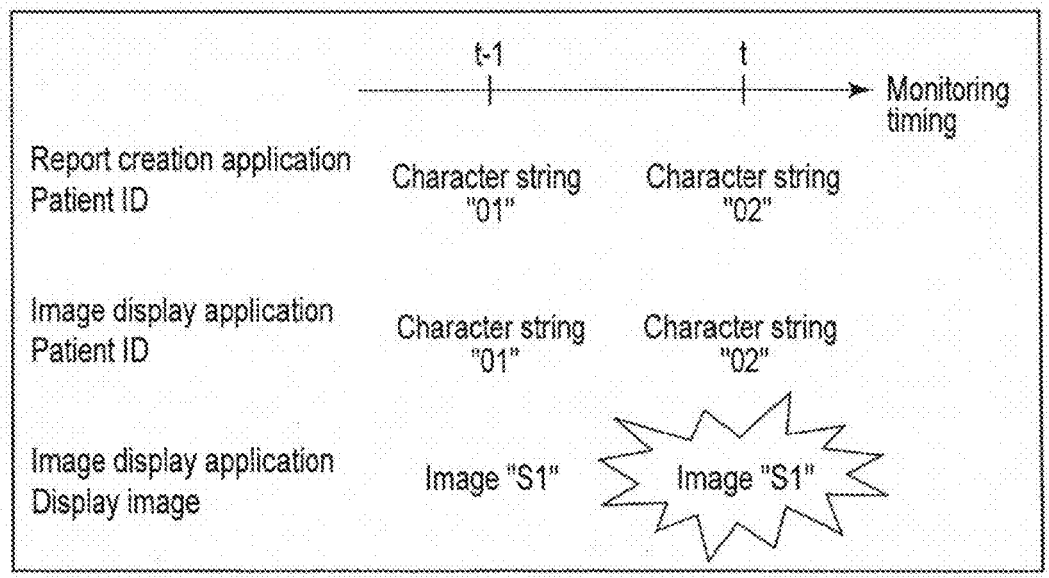
F I G. 7

MEDICAL INFORMATION MANAGEMENT DEVICE

CROSS-REFERENCE TO RELATED APPLICATIONS

This application is based upon and claims the benefit of priority from Japanese Patent Applications No. 2012-070047, filed Mar. 26, 2012; and No. 2013-033757, filed Feb. 22, 2013, the entire contents of all of which are incorporated herein by reference.

FIELD

Embodiments described herein relate generally to a medical information management device.

BACKGROUND

There is a medical image diagnostic system including a medical image capturing device, a medical image storage device, an interpretation report creation and support system, and an electronic chart system connected via a network. A user performs, on a client terminal, diagnostic work using a medical application provided by the medical image diagnostic system. Specific examples of the medical application used for the diagnostic work may include an image display application, a report creation application, and an electronic chart creation application.

Multiple types of information are displayed in the medical application. When the diagnostic work is performed on a certain patient, all of the multiple types of displayed information are generally information on the same patient. For example, patient information (e.g., name, birth date, sex and age), examination information (e.g., examination date and examination classification), image information (e.g., an examination image acquired by a medical image acquiring device), and the like are displayed on a screen of the image display application. If the user performs the diagnosis of patient A at a certain time point, the patient information, the examination information, and the image information should be displayed as information on patient A.

In addition, there is a case in which diagnostic work is performed using a plurality of medical applications. In this case, a plurality of screens respectively corresponding to the medical applications is displayed on a client terminal or the like. Information on the same patient should be basically displayed in all of the screens. For example, if a screen of an image display application, a screen of a report creation application, and a screen of an electronic chart display application are displayed and a user is performing the diagnosis of patient A, the information on patient A should be displayed on all the screens.

However, matching of information in one medical application or matching of information in a plurality of medical applications may collapse due to a faulty operation of the medical application, an unexpected user manipulation, or the like. For example, in an image display application, if a diagnosis target is changed from patient A to patient B, patient information is changed to information on patient B, but an examination image may not be changed to an image of patient B and remain as the image of patient A. Such collapse of the matching is laden with risk of causing misdiagnosis.

An object is to provide a medical information management device that allows accuracy of diagnostic work using a medical application to be improved.

BRIEF DESCRIPTION OF THE DRAWINGS

FIG. 3 is a diagram illustrating a functional configuration of a processing unit of FIG. 2;

FIG. 4 is a diagram for explaining a process of setting a monitoring item in a monitoring item setting unit of FIG. 3 and is a diagram illustrating an example of a screen of a report creation application;

FIG. 5 is a diagram for explaining a process of setting a monitoring item in a Rule setting unit of FIG. 3, and is a diagram illustrating an example of a screen of a report creation application and a screen of an image display application;

FIG. 6 is a diagram for specifically explaining a determination process in a determination unit of FIG. 3;

FIG. 7 is another diagram for specifically explaining a determination process in a determination unit of FIG. 3;

DETAILED DESCRIPTION

In general, according to one embodiment, a medical information management device includes a display unit, an acquisition unit, a determination unit, and alerting unit. The display unit displays a screen of a medical application. The acquisition unit acquires a plurality of values used in the medical application and belonging respectively to a plurality of monitoring items set in advance. The determination unit determines whether the acquired values satisfy a matching determination rule for relevance of presence or absence of a change in a value of a reference item among a plurality of monitoring items in the medical application and presence or absence of a change in a value of the other item. The alerting unit controls the display unit to display an alert when it is determined by the determination unit that the acquired values do not satisfy the matching determination rule.

A medical information management device according to the present embodiment will be described with reference to the accompanying drawings.

Figure 1:
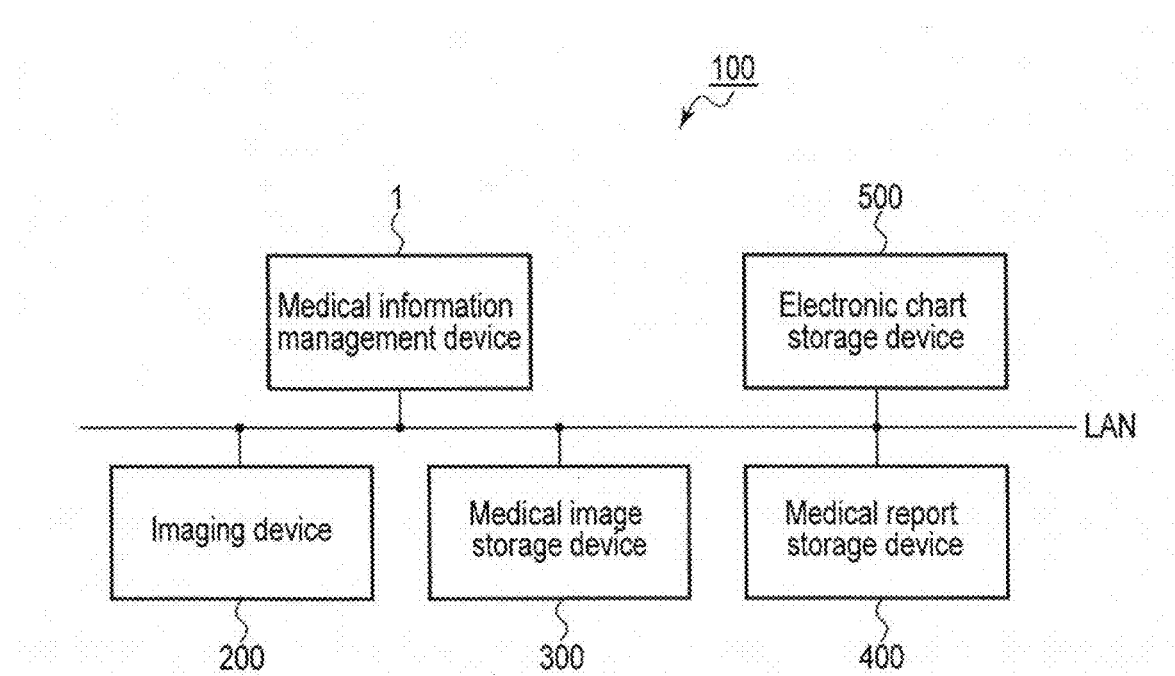
FIG. 1 is a diagram illustrating a network environment of a medical information management device according to the present embodiment.

FIG. 1 is a diagram illustrating a network environment of the medical information management device 1 according to the present embodiment. As shown in FIG. 1, the medical information management device 1 is connected to an imaging device 200, a medical image storage device 300, a medical report storage device 400, and an electronic chart storage device 500 via a network (LAN). The medical information management device 1, the imaging device 200, the medical image storage device 300, the medical report storage device 400, and the electronic chart storage device 500 constitute a medical image diagnostic system 100. The medical information management device 1 functions as a thin client terminal that remotely uses hardware resources such as the imaging device 200, the medical image storage device 300, the medical report storage device 400, and the electronic chart storage device 500 via the LAN.

The imaging device 200 performs medical imaging for the inside of a body of a patient or the like through examination to generate medical image data about the patient. The medical image data is transmitted to the medical image storage device 300 in a format conforming to a DICOM (Digital Imaging and Communications in Medicine) standard.

The medical image storage device 300 stores the medical image data from the imaging device 200. In addition, the medical image storage device 300 manages patient information, examination information, and image information associated with the medical image data in a database. For example, the medical image storage device 300 executes an image display application according to an instruction from the medical information management device 1, and transmits data and logic of a screen of an image display application to the medical information management device 1.

The medical report storage device 400 stores a medical report created by the medical information management device 1 or the like. For example, the medical report storage device 400 executes a report creation application according to an instruction from the medical information management device 1, and transmits data and logic of a screen of the report creation application to the medical information management device 1.

The electronic chart storage device 500 stores the electronic chart created by the medical information management device 1 or the like. For example, the electronic chart storage device 500 executes an electronic chart display application according to an instruction from the medical information management device 1 and transmits data and logic of a screen of the electronic chart display application to the medical information management device 1.

The medical information management device 1 logs into the medical image storage device 300, the medical report storage device 400 or the electronic chart storage device 500 via the LAN and executes the medical application installed on the device 300, 400 or 500 to which it has logged in. The screen of the medical application from the medical image storage device 300, the medical report storage device 400 or the electronic chart storage device 500 is displayed on a display device of the medical information management device 1. Examples of the medical application may include an image display application, a report creation application, and an electronic chart display application. Each medical application may be subdivided into a plurality of applications. For example, the image display application is also subdivided into a 2D image display application or a 3D image display application. The same types of applications may be provided to the medical information management device 1 by a plurality of manufacturers. The user performs medical work according to the medical application executed in the medical information management device 1 while observing the screen.

Figure 2:
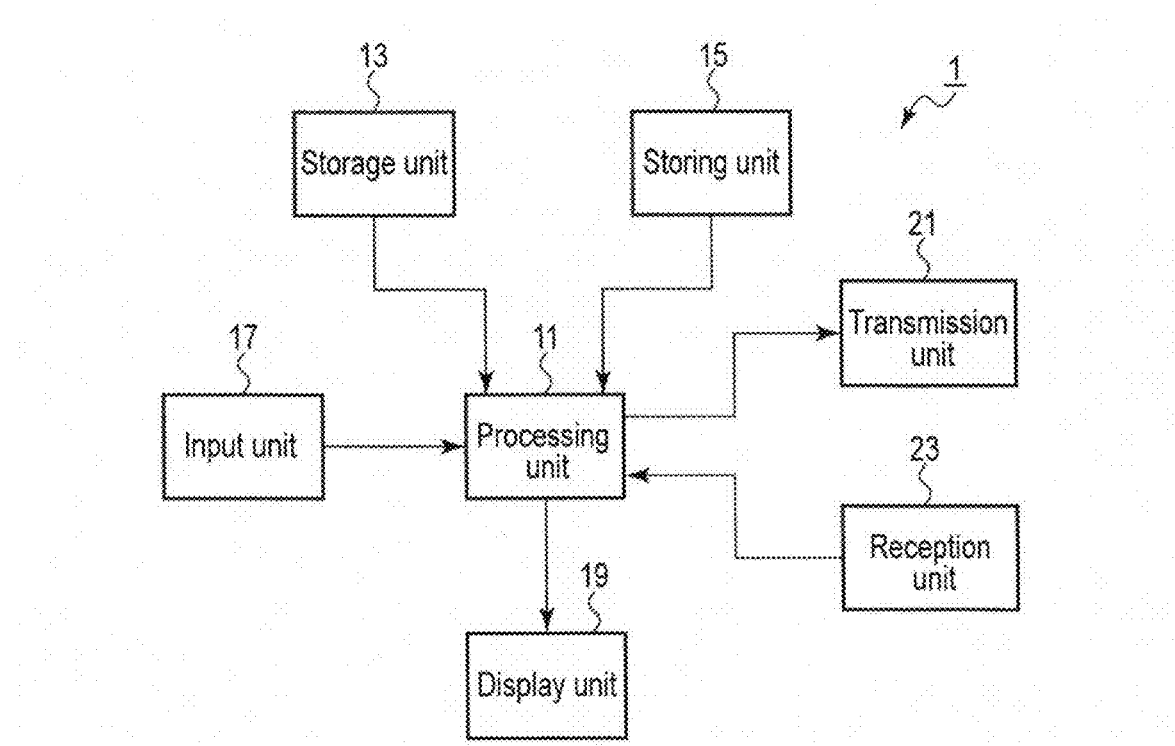
FIG. 2 is a diagram illustrating a hardware configuration of the medical information management device of FIG. 1.

FIG. 2 is a diagram illustrating a hardware configuration of the medical information management device 1. As shown in FIG. 2, the medical information management device 1 includes a storage unit 13, a storing unit 15, an input unit 17, a display unit 19, a transmission unit 21, and a reception unit 23 around a processing unit 11.

The storage unit 13 is a storage device including storage media such as a RAM and a ROM. For example, the storage unit 13 is used as a work area by the processing unit 11. In other words, the storage unit 13 is used to temporarily store data generated by processing in the processing unit 11.

The storing unit 15 is a storage device including a storage medium for long-term storage, such as an HD (Hard Disk Drive). For example, the storing unit 15 stores medical image data from the medical image storage device 300, the medical report from the medical report storage device 400, and the electronic chart from the electronic chart storage device 500.

The input unit 17 receives various instructions and information input from the user via an input device. The input unit 17 transmits an input signal corresponding to an input manipulation of the input device by the user to the processing unit 11. The input device may include a pointing device such as a mouse or a trackball, a selection device such as a switch button, a keyboard, or the like.

The display unit 19 includes an image synthesis circuit, a VRAM (Video Random Access Memory), and a display device. The display unit 19 displays screens of one or a plurality of medical applications input via the reception unit 23 on the display device. When the screens of the medical applications are displayed, the screens may be displayed separately on different display devices or may be displayed in parallel on the same display device. Examples of the display device may include a CRT display, a liquid crystal display, an organic EL display, a plasma display and the like.

The transmission unit 21 transmits instructions and various medical data to the medical image storage device 300, the medical report storage device 400 or the electronic chart storage device 500. For example, the transmission unit 21 transmits an input signal corresponding to an input manipulation of the input unit 17 by the user to the medical image storage device 300, the medical report storage device 400 or the electronic chart storage device 500. Further, the transmission unit 21 transmits various medical data generated by the processing unit 11 to the medical image storage device 300, the medical report storage device 400 or the electronic chart storage device 500. Further, the transmission unit 21 transmits a transmission request for various medical data to the medical image storage device 300, the medical report storage device 400 or the electronic chart storage device 500.

The reception unit 23 receives the data and logic of the screen of the medical application from the medical image storage device 300, the medical report storage device 400 or the electronic chart storage device 500. Further, the reception unit 23 receives various medical data transmitted from the medical image storage device 300, the medical report storage device 400 or the electronic chart storage device 500 in response to a transmission request.

The processing unit 11 is a control device functioning as a center of the medical information management device 1. The processing unit 11 includes an integrated circuit enclosed in a package in which an electronic circuit made of a semiconductor includes a plurality of terminals. The processing unit 11 executes a program stored in the storage unit 13 using the input of a start instruction by the user via the input unit 17 as a trigger. The processing unit 11 displays various pieces of information for the user on the display unit 19 using graphics. The processing unit 11 provides a GUI (Graphical user Interface) in which a basic manipulation can be performed by the input unit 17.

Further, the processing unit 11 executes an application for monitoring the matching of information (hereinafter referred to as a monitoring application) in one medical application or among a plurality of medical applications at a default monitoring timing. For example, the monitoring application is stored in the storage unit 13. If it is determined that the matching of the information has collapsed, the processing unit 11 alerts the user using the display unit 19. Accordingly, the user can recognize an abnormal condition, thereby preventing misdiagnosis that may be caused by an abnormal state of the application. The processing unit 11 can mitigate effects of an abnormal situation. Here, the monitoring refers to acquiring a value of information of a monitoring target and confirming matching of the value and a value of other information at the monitoring timing. A specific operation example of the processing unit 11 executing the monitoring application will be described.

FIG. 3 is a diagram illustrating a functional configuration of the processing unit 11 by execution of the monitoring application. As shown in FIG. 3, the processing unit 11 includes a monitoring item setting unit 31, a monitoring timing setting unit 33, a Rule setting unit 35, an acquisition unit 37, a determination unit 39, and an alerting unit 41.

The monitoring item setting unit 31 may set a plurality of monitoring items from information used in the one or the plurality of medical applications displayed by the display unit 19 according to an instruction from the user. The monitoring item may be arbitrarily selected from among all information displayed or managed by the medical application. For example, the monitoring item is appropriately selected from among information items displayed on the screen of the medical application, and the information items internally managed by the medical application. Specifically, the information items internally managed by the medical application are not displayed on the screen, but are information items used by the medical application. Further, in the present embodiment, the monitoring item refers to a combination of a type of the medical application and the information item. That is, if medical applications to which the information items belong are different even though the information items are of the same type, the monitoring items are assumed to be different monitoring items. For example, when patient information of the report creation application and patient information of the image display application are set as monitoring items, the two monitoring items are assumed to be different monitoring items. Identifiers of the monitoring items are supplied to the acquisition unit 37.

FIG. 4 is a schematic diagram of a screen (the report creation screen) RI of the report creation application. Display items of the report creation screen RI of FIG. 4 include display items of patient information, finding, diagnosis, a past report list, and a past report. In addition, the patient information is subdivided into items such as patient ID, name, date of birth, and sex. The monitoring item setting unit 31 may set such information as the monitoring items. One type of information may be set as the monitoring item or multiple types of information may be set as the monitoring items. For example, only the patient ID may be set as the monitoring item or three types of information of the patient ID, the finding and the diagnosis may be set as the monitoring items. A value of the monitoring item is typically a character string belonging to the monitoring item. For example, if the monitoring item is the patient ID, the value that the patient ID has is "0001." If the monitoring item is an image such as an examination image, the value of the monitoring item is image data. In the present embodiment, the image data is an enumeration of discrete values (typically 0 and 1) constituting the image data.

Specifically, a value of the item "finding" is "Ascites is observed around the stomach and intestinal tract and is slightly increasing." A value of the item "diagnosis" is "Middle bile duct cancer surgery: a hole is suspected to be formed in a front inferior vena cava." A value of the item "examination date" is "Feb. 5, 2010" "Feb. 10, 2010," or "Feb. 15, 2010."

The monitoring item is not a minimum element of information displayed on a screen of the medical application, such as "patient ID" and may be set as information including multiple types of sub-items such as "patient information." In the case of the monitoring item including multiple types of sub-items, the value of the monitoring item may be all character strings belonging to the sub-items or may be captured image data limited to a local display area LS1 of the monitoring item in the screen. For example, if the monitoring item is "patient information" in FIG. 4, the value of the monitoring item may be all character strings of patient ID, name, date of birth and sex, i.e., "0001," "Toshiba Taro," "Jan. 1, 1997", and "male" or may be the captured image data of the local display area LS1. The monitoring item is typically set by the service engineer.

Settings of the monitoring item may be stored in the medical information management device 1 in various forms. The settings of the monitoring item may be stored outside the monitoring application or may be stored in the monitoring application. If the settings of the monitoring item are stored outside the monitoring application, for example, the settings of the monitoring item may be stored in the storing unit 15 as a setting file or may be stored as the DB (Data Base) in the storing unit 15. If the settings of the monitoring item are stored inside the monitoring application, the settings of the monitoring item are stored by being incorporated in an internal algorithm of the monitoring application.

The monitoring timing setting unit 33 sets a monitoring timing of the monitoring item set by the monitoring item setting unit 31. Specifically, the monitoring timing is a timing at which the acquisition unit 37, which will be described below, acquires the value of the monitoring item. An identifier of the monitoring timing is supplied to the acquisition unit 37.

The monitoring timing may include three types below. Type 1. "Every unit time such as every 10 seconds," type 2. "When the medical application becomes active," and type 3. "When a display instruction for a medical application is made via the input 17 by the user." Further, in the case of type a specific numerical value of the unit time may be arbitrarily set by the user via the input unit 17. The monitoring timing may be set to any one of the three types or the three types may be appropriately combined. For example, the monitoring timing may be a combination of the time point at which the medical application becomes active and every unit time. The monitoring timing may be set as the monitoring timing of an appropriate type according to the monitoring item. The monitoring timing may be arbitrarily set by the user via the input unit 17 in consideration of a load of the device or the like. The monitoring timing is typically set by a service engineer. However, the monitoring timing may also be automatically set according to the monitoring item set by the monitoring item setting unit 31 using a LUT (Look Up Table) in which the monitoring item and the monitoring timing are associated.

Settings of the monitoring timing may be stored in the medical information management device 1 in various forms. The settings of the monitoring item may be stored outside the monitoring application or may be stored inside the monitoring application. If the settings are stored outside the monitoring application, for example, the settings of the monitoring timing may be stored in the storing unit 15 as a setting file or may be stored as a DB (Database) in the storing unit 15. If the settings are stored inside the monitoring application, the settings are stored by being incorporated in an internal algorithm of the monitoring application.

The Rule setting unit 35 sets a matching determination rule for a plurality of monitoring items set by the monitoring item setting unit 31. A different type of matching determination rule is used according to a dependency relationship between the monitoring items. The matching determination rule defines a relevance of presence or absence of a change in a value of a reference item among the monitoring items and presence or absence of a change in a value of another item. For example, the matching determination rule is typically type 1

"A value of a monitoring item that is a reference and a value of the other monitoring item should be the same," and type 2 "When a value of a monitoring item that is a reference is changed, a value of the other monitoring item should also be changed." Whether the matching determination rule of type 1 or the matching determination rule of type 2 is used may be arbitrarily set by the user or a service engineer via the input unit 17. Both the matching determination rule of type 1 and the matching determination rule of type 2 may be used. The matching determination rule may be set for each monitoring item or one matching determination rule may be set for a plurality of monitoring items. The matching determination rule may be arbitrarily set by the user or the service engineer via the input unit 17. The matching determination rule is typically set by the service engineer. However, the matching determination rule may be set automatically according to a monitoring item set by the monitoring item setting unit 31 using a LUT (Look Up Table) in which the monitoring item and the matching determination rule are associated.

The matching determination rule of type 1 is used to determine whether matching of the monitoring item among a plurality of medical applications is satisfied. Specifically, the matching determination rule of type 1 is a determination rule for confirming that the information displayed on the screens of a plurality of medical applications is information of the same patient. The matching determination rule of type 1 will be described in detail with reference to FIG. 5.

FIG. 5 is a diagram illustrating an example of the screen (report creation screen) RI of the report creation application and the screen (hereinafter, an image display screen) II of the image display application. In work of creating the medical report, typically, the report creation screen RI and the image display screen II are separately displayed on different display devices. The user creates a medical report with reference to the report creation screen RI and the image display screen II.

As shown in FIG. 5, a patient ID is displayed on both of the report creation screen RI and the image display screen II. The patient ID displayed on the report creation screen RI and the patient ID displayed on the image display screen II should always be the same. This is because the patient ID displayed on the report creation screen RI and the patient ID displayed on the image display screen II being different means that the patients displayed by the two applications differ. That is, if the patient IDs displayed in the two applications differ, a user is likely to observe an examination image of a different patient from a patient of a diagnosis target and make misdiagnosis. To prevent such misdiagnosis, a matching determination rule "a character string of the patient ID displayed on the report creation screen and a character string of the patient ID displayed on the image display screen should be always the same" may be set. It is ensured that information displayed on the report creation screen RI and the image display screen II is always information on the same patient by confirming whether the matching determination rule is satisfied.

The matching determination rule of type 2 is used to determine whether the matching of the monitoring item is satisfied in the one medical application. The matching determination rule of type 2 is a determination rule for confirming that information displayed on the screen of the one medical application is the information on the same patient.

For example, patient information displayed in a patient information column of the report creation display screen RI and finding information displayed in a finding column should always be information of the same patient. However, there are cases in which the patient information and the finding information may be information on different patients due to incorrect operation of the medical application. If the information on the different patients is displayed in a plurality of display items on the screen of the one medical application as described above, it is highly likely for the user to make misdiagnosis. To prevent such misdiagnosis, a matching determination rule "If a character string of the patient ID displayed on the report creation screen is changed, a character string of the finding displayed on the report creation screen should be changed" may be set. It is ensured that information displayed in the display items in the report creation screen has been changed at an appropriate timing by confirming whether such a matching determination rule is satisfied.

Settings of the matching determination rule may be stored in the medical information management device 1 in various forms. The settings of the monitoring item may be stored outside the monitoring application or may be stored inside the monitoring application. If the settings of the monitoring item are stored outside the monitoring application, for example, the settings of the matching determination rule may be stored in the storing unit 15 as a setting file or may be stored as a DB (Database) in the storage unit 15. If the settings of the monitoring item are stored inside the monitoring application, the settings of the monitoring item are stored by being incorporated in an internal algorithm of the monitoring application.

The acquisition unit 37 acquires a plurality of values belonging to a plurality of monitoring items set by the monitoring item setting unit 31 in advance, which are used in one or a plurality of medical applications, at a monitoring timing set by the monitoring timing setting unit 33 in advance. For example, when the monitoring timing is every unit time, the acquisition unit 37 periodically acquires the value of the monitoring item every unit time. Examples of a method of acquiring the value of each monitoring item include three methods below. Any one of the three acquisition methods below to be adopted may be arbitrarily set by the user via the input unit 17. The acquisition method may be set for each monitoring item or may be set for each medical application to which the monitoring item belongs.

Acquisition method 1: Acquisition method 1 is a method by which the acquisition unit 37 receives the value of the monitoring item actively sent by the medical application. In this case, the medical application sends the value of the monitoring item to the acquisition unit 37 at a monitoring timing. The sent value is received by the acquisition unit 37.

Acquisition method 2: Acquisition method 2 is a method by which the acquisition unit 37 acquires a value of a monitoring item using an application interface for acquiring a value of a monitoring item (hereinafter, a value acquisition application interface). If the medical application has a value acquisition application interface mounted thereon, the acquisition unit 37 acquires the value of the monitoring item using the value acquisition application interface at a monitoring timing. For example, the value acquisition application interface is realized by a specific function housed in a library function. In this case, the acquisition unit 37 executes a function for value acquisition and acquires a returned value of the executed function as the value of the monitoring item at the monitoring timing.

Acquisition method 3: Acquisition method 3 is a method of acquiring a value of a monitoring item by image-analyzing a captured image of the screen of the medical application. In this case, the acquisition unit 37 generates image data of a local display area including a display area of the monitoring item in the screen of the medical application using a screen shot function at a monitoring timing. Also, the acquisition unit 37 image-analyzes the image data of the generated local display area, and recognizes the value of the monitoring item included in the image data. Acquisition method 3 may be used when it is difficult to adopt acquisition method 1 and acquisition method 2 described above. For example, if the character string of the patient ID is acquired from a report creation application of another company, it is difficult to implement functions of acquisition methods 1 and 2 described above in the report creation application of the other company. In this case, the acquisition unit 37 generates image data of the local display area including the character string of the patient ID displayed on the screen of the report creation application, and recognizes characters of a character string included in the generated image data to acquire the character string of the patient ID.

The determination unit 39 determines whether a plurality of values respectively corresponding to a plurality of monitoring items acquired by the acquisition unit 37 satisfy the matching determination rule. If the values do not satisfy the matching determination rule, it means that the matching has collapsed, and if the values satisfy the matching determination rule, it means that the matching is maintained.

Hereinafter, a determination process in the determination unit 39 will be described in detail with reference to and FIGS. 6 and 7. Further, in the following specific example, the monitoring item is assumed to be a patient ID of the report creation application, a patient ID of the image display application, and an image display area of the image display application. Further, the matching determination rule is assumed to be matching determination rule 1 "A character string of a patient ID of the report creation application and a character string of a patient ID of the image display application should be the same" and matching determination rule 2 "when the character string of the patient ID of the image display application is changed, an image displayed in the image display area of the image display application (hereinafter referred to as a display image) should be changed."

As shown in FIG. 6, it is assumed that the value (the character string) of the monitoring item "the patient ID of the report creation application" is "01," the value (the character string) of the monitoring item "the patient ID of the image display application" is "01," and the value (image data) of the monitoring item "the display image of the image display application" is "S1" at the monitoring timing t−1. In addition, it is assumed that the value (the character string) of the monitoring item "the patient ID of the report creation application" is "02," the value (the character string) of the monitoring item "the patient ID of the image display application" is "01," and the value (image data) of the monitoring item "the display image of the image display application" is "S2" at a next monitoring time t after the monitoring timing t−1. In this case, since the character string of the patient ID of the report creation application and the character string of the patient ID of the image display application differ at the monitoring time t, matching determination rule 1 described above is not satisfied at the monitoring timing t. Accordingly, the determination unit 39 can correctly determine that the matching of the information is not satisfied between the monitoring item "the patient ID of the image display application" and the monitoring item "the patient ID of the report creation application" at the monitoring time t.

Further, a state shown in FIG. 7 is considered as a second specific example. In FIG. 7, it is assumed that the value (the character string) of the monitoring item "the patient ID of the report creation application" is "02," the value (the character string) of the monitoring item "the patient ID of the image display application" is "02," and the value (image data) of the monitoring item "the display image of the image display application" is "S1" at the monitoring timing t. In this case, the character string of the patient ID of the report creation application at the monitoring time t is changed from "01" to "02," but the display image of the image display application remains "S1" without being changed, and matching determination rule 2 is not satisfied at the monitoring timing t. Accordingly, the determination unit 39 can correctly determine that the matching of the information is not satisfied between the monitoring item "the patient ID of the image display application" and the monitoring item "the patient ID of the report creation application" at the monitoring time t.

If it is determined by the determination unit 39 that the matching determination rule is not satisfied, the alerting unit 41 transmits an alerting signal to the display unit 19 in order to display an alert on the display unit 19. The display unit 19 displays the alert that the matching determination rule is not satisfied in response to the alerting signal. For example, a dialog box may be displayed as an alert display. Further, as another example of the alert display, a local display area for the monitoring item for which the matching determination rule is not satisfied in the screen of the medical application and the other display area may be displayed visually distinctly. For example, the local display area for the monitoring item for which the matching determination rule is not satisfied may be displayed to be highlighted relative to the remaining display area. On the other hand, if it is determined by the determination unit 39 that the matching determination rule is satisfied, the alerting unit 41 transmits a non-alerting signal the display unit 19 in order not to display the alert on the display unit 19. The display unit 19 receiving the non-alerting signal does not alert and displays the screen of the medical application in a normal layout. Alternatively, when receiving the non-alerting signal, the display unit 19 may display the fact that the matching is satisfied. Further, if it is determined by the determination unit 39 that the matching determination rule is satisfied, the alerting unit 41 may transmit no signal to the display unit 19. In this case, the display unit 19 does not display the alert as long as the alerting signal is not sent.

Figure 8:
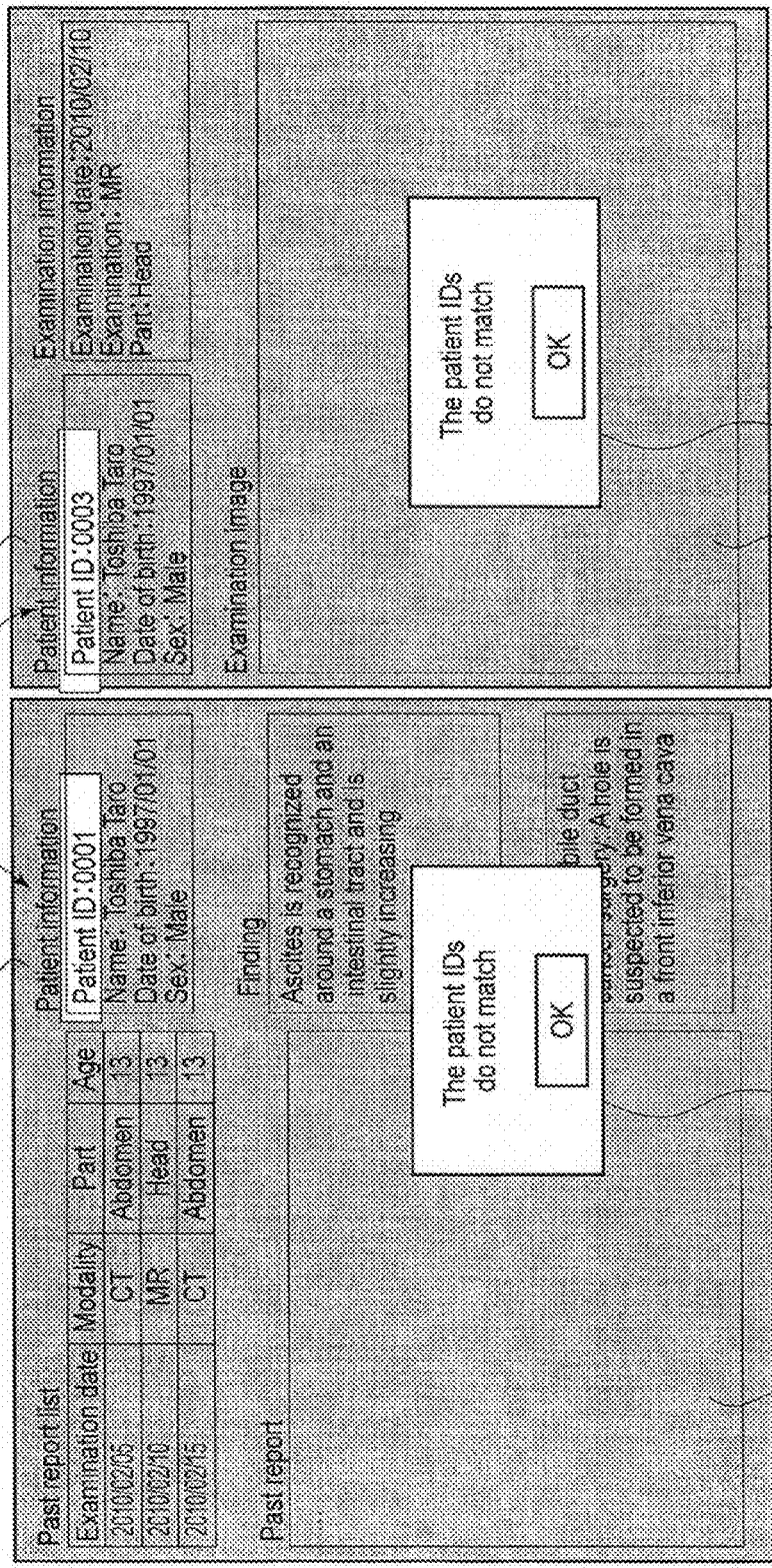
FIG. 8 is a diagram illustrating an example of an alerting process in an alerting unit of FIG. 3.

FIG. 8 is a diagram illustrating an example of an alert display. FIG. 8 shows an alert display example in which the matching determination rule "a character string of a patient ID of a report creation application and a character string of a patient ID of an image display application should be the same" is not satisfied. As shown in FIG. 8, the character string ("0001") of the patient ID of the report creation screen RI and the character string ("0003") of the patient ID of the image display screen II differ. Therefore, in this case, the matching determination rule is not satisfied. If it is determined that the matching determination rule is not satisfied, the display unit 19 displays a dialog box DB for an alert on each of the report creation screen RI and the image display screen II. A message indicating that the matching determination rule is not satisfied, such as "The patient IDs do not match" may be displayed in the dialog box DB. The display unit 19 erases the dialog box DB from the screens RI and II using pressing of an "OK" button in the dialog box DB by the user via the input unit 17 as a trigger. In addition, the dialog box DB may be displayed on only any one of the report creation screen RI and the image display screen II. Further, the dialog box DB may be displayed across both the report creation screen RI and the image display screen II using multi-monitor technology.

Further, the display unit 19 may display only a highlighted area TR of the report creation screen RI and a highlighted area TR of the image display screen II as usual, and may mask the remaining display area NR. Further, the highlighted area TR corresponds to a display area limited to the monitoring item in the screens RI and II. In the case of FIG. 8, since the monitoring item is set as "patient ID," the highlighted area TR has been set to the display area limited to the patient ID. For example, the other display area NR may be covered with a specified translucent color (for example, gray). Thus, the display area TR for the monitoring item in which the matching determination rule is not satisfied and the other display area NR may be displayed visually distinctly. Further, the specified color may be set to any color by the user via the input unit 17. Further, a transparency degree of the mask may be set to any value by the user via the input unit 17.

Another use example of the monitoring application may include a comparison of past examination and current examination of the same patient. Hereinafter, a use example of the monitoring application in the comparison will be described. Further, in order to specifically perform the following description, a comparison of a report on the past examination (hereinafter referred to as a past report) and a report on the current examination (hereinafter referred to as current report) will be described by way of example.

Figure 9:
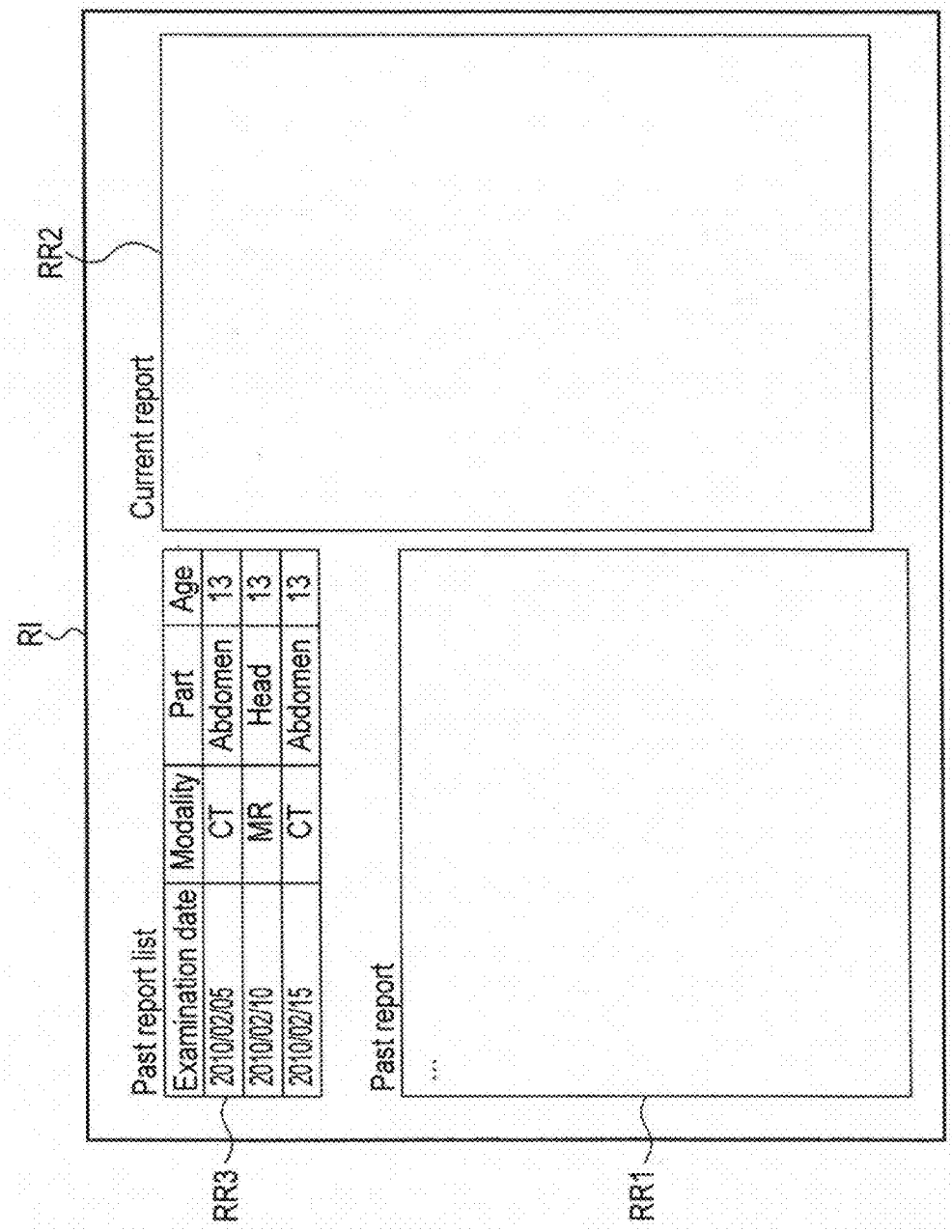
FIG. 9 is a diagram illustrating one example of operation of the medical information management device of FIG. 2 and is a diagram illustrating an example of a screen for comparison of a past report and a current report.

FIG. 9 is a diagram that illustrates a screen example for a comparison of the past report and the current report. As shown in FIG. 9, a display area RR1 for the past report, a display area RR2 for the current report, and a display area RR3 for a list of past reports are included in a screen RI. In the display area RR3, records about the past reports are displayed as a list. Each record includes items about examination information such as examination date, modality, part and age about past examinations. The display area RR1 is set as a monitoring item by the monitoring item setting unit 31. A value of the monitoring item "display area RR1" is data of the past report. Here, the monitoring item "display area RR1" is assumed to be a comparison item.

In the comparison, the user specifies a record of a display target from a plurality of records in the display area RR3 via the input unit 17.

In a normal state, the display unit 19 displays the past report on the specified record in the display area RR1 using specifying of a record of the display target as a trigger. However, there are cases in which the past report on the specified record is not displayed even when the record of the display target is specified. In such an abnormal state, the user may mistake the report displayed in the display area RR1 for the past report on the specified record.

The medical information management device 1 according to the present embodiment can detect a defect in which specifying of the record is not reflected on the display area RR1, using the monitoring application.

First, the monitoring item setting unit 31 sets the record specified via the input unit 17 as the monitoring item. For example, a value of the monitoring item "record specified via the input unit 17" is a character string belonging to the record. The monitoring item "record specified via the input unit 17" is assumed to be a reference item. The monitoring timing is set as "when any one of a plurality of reports displayed in the display area RR3 is specified via the input unit 17" by the monitoring timing setting unit 33. The acquisition unit 37 acquires a value of the reference item and a value of a comparison item at the monitoring timing. The matching determination rule is set as the above-described type 2 "When a value of a monitoring item that is a reference is changed, a value of the other monitoring item should also be changed" by the Rule setting unit 35. The determination unit 39 determines whether the value of the reference item and the value of the comparison item satisfy the matching determination rule of type 2.

For example, it is assumed that the monitoring timing t−1 is when a previous record selection is made and the monitoring timing t is when a current record selection is made. In this case, the acquisition unit 37 acquires the value of the reference item and the value of the comparison item at each of the monitoring timing t and the monitoring timing t−1. The determination unit 39 compares the value of the reference item at the monitoring timing t−1 with the value of the reference item at the monitoring timing t to determine whether the value of the reference item has been changed. Similarly, the determination unit 39 compares the value of the comparison item at the monitoring timing t−1 with the value of the comparison item at the monitoring timing t to determine whether the value of the comparison item has been changed. Also, when the value of the comparison item has been changed but the value of the reference item has not been changed, the determination unit 39 determines that the matching determination rule is not satisfied. Otherwise, the determination unit 39 determines that the matching determination rule is satisfied.

If it is determined by the determination unit 39 that the matching determination rule is not satisfied, the alerting unit 41 transmits an alerting signal to the display unit 19 in order to display an alert on the display unit 19. The display unit 19 displays the alert indicating that the matching determination rule is not satisfied in response to the alerting signal. The display unit 19 displays the alert that the matching determination rule is not satisfied in response to the alerting signal. On the other hand, if it is determined by the determination unit 39 that the matching determination rule is satisfied, the alerting unit 41 transmits a non-alerting signal to the display unit 19 in order not to display the alert on the display unit 19. The display unit 19 receiving the non-alerting signal does not alert and displays the screen of medical application in a normal layout.

Through the above-described operation, it is possible to detect the defect in which specifying of the record is not reflected on the display area of the past examination record.

This concludes the description of the specific operation example of the processing unit 11.

Further, in the foregoing description, the medical information management device 1 is assumed to be the thin client terminal that remotely uses, via the LAN, the medical applications installed in the various devices 200, 300, 400 and 500 connected via the network. However, the medical information management device 1 according to the present embodiment is not limited thereto. That is, the medical application may also be installed in the medical information management device 1. In this case, the medical application is executed, for example, by the processing unit 11.

That is, the medical information management device may not be the thin client terminal. For example, the medical information management device 1 may be a viewer. In this case, the image display application is installed in the medical information management device 1. The medical information management device 1 may also be a report creation device. In this case, a report creation application is installed in the medical information management device 1. A medical application that can be installed in the medical information management device 1 is not limited to one type, and a plurality of medical applications may be installed in the medical information management device 1.

Further, the medical information management device 1 according to the present embodiment may be a monitoring device. The monitoring device makes a technical matching determination using the aforementioned monitoring application without performing a remote manipulation or a direct manipulation of the medical application. In other words, the monitoring device includes the processing unit 11 and is connected to the other medical device performing the execution of the medical application via a network. The monitoring device receives data from the other medical device. Also, using the monitoring application, the monitoring device determines the matching of the information of the medical application that is used or executed by the other medical device, based on the received data. Accordingly, it is possible to reduce time and effort to install the monitoring application in the client terminal.

Further, the monitoring application may be installed in the imaging device 200, the medical image storage device 300, the medical report storage device 400, or the electronic chart storage device 500. In other words, the above-described monitoring device may be incorporated into the imaging device 200, the medical image storage device 300, the medical report storage device 400 or the electronic chart storage device 500.

According to the foregoing description, the medical information management device 1 according to the present embodiment includes the display unit 21, the acquisition unit 37, the determination unit 39, and the alerting unit 41. The display unit 21 displays the screen of the medical application. The acquisition unit 37 acquires a plurality of values of a plurality of monitoring items set in advance, which is used in the medical application, at a monitoring timing set in advance. The determination unit 39 determines whether the acquired values satisfy the matching determination rule. The matching determination rule defines the relevance of the presence or absence of a change in the value of the reference item and the presence or absence of a change in the value of another item among the monitoring items in the medical application. If it is determined that the matching determination rule is satisfied, the alerting unit 41 does not display the alert on the display unit 21, and if the matching determination rule is not satisfied, the alerting unit 41 controls the display unit 21 to display the alert.

By this configuration, the medical information management device 1 can alert the user when matching between information displayed in the one medical application or matching of information displayed in a plurality of medical applications has collapsed. Thus, it is possible to inform the user of generation of a dangerous condition that leads to misdiagnosis and to preemptively prevent misdiagnosis.

Thus, according to the present embodiment, it is possible to improve the accuracy and efficiency of diagnostic work using the medical application.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information management device comprising:
a display circuitry configured to display a screen of a medical application;
a monitoring item setting circuitry configured to set a plurality of monitoring items from among information items used in the medical application;
an acquisition circuitry configured to acquire a value belonging to the plurality of monitoring items set by the monitoring item setting circuitry;
a determination circuitry configured to determine whether the value acquired by the acquisition circuitry follows at least one of a first and second matching determination rules corresponding to the medical application, the first matching determination defining that values acquired from monitoring items relevant to each other should be the same, the second matching determination defining that, in response to a change of a value acquired from a reference item set among the plurality of monitoring items, a value acquired from a monitoring item relevant to the reference item should change; and
an alerting circuitry configured to control the display circuitry to display alert in response to a determination, by the determination unit, that the value acquired by the acquisition circuitry do not follow at least one of the first and second matching determination rule.

2. The medical information management device according to claim 1, wherein:
the determination circuitry determines, if the medical application includes one medical application, whether the value acquired from a monitoring item within the one medical application follows the second matching determination rule or not, and
the determination circuitry determines, if the medical application includes a plurality of medical applications, whether the values acquired from monitoring items relevant to each other between the plurality of medical applications follow the first matching determination rule or not.

3. The medical information management device according to claim 1, wherein the values are a character displayed on the screen, image data displayed on the screen, and a set value of the medical application.

4. The medical information management device according to claim 1, further comprising a timing setting circuitry that sets a timing of the acquisition circuitry to acquire the value.

5. The medical information management device according to claim 4, wherein the timing is at least one of every unit time, a time point at which the medical application becomes active, and a time point at which a display instruction for the medical application is made according to an instruction from a user.

6. The medical information management device according to claim 1, wherein the acquisition circuitry acquires the values using at least one of reception of the values of the monitoring items actively sent by the medical application, use of a library function belonging to the medical application, and analysis of a capture image of a screen of the medical application.

7. The medical information management device according to claim 1, wherein, the alerting circuitry controls the display circuitry to display an alerting dialog box on the screen.

8. The medical information management device according to claim 1, the alerting circuitry controls the display circuitry to visually distinctly display a first display area for a monitoring item of which a value do not follow at least one of the first and second matching determination rule in the screen, and a second display area excluding the first display area.

9. The medical information management device according to claim 1, wherein:
the medical application includes a display application for past examination and a display application for a list of past examinations, and
the monitoring item setting circuitry sets, as the monitoring items, user-specified past examination record among a plurality of past examination records displayed in a display area for the display application of past examination, and examination displayed in a display area of the display application for a list of the past examinations.

10. The medical information management device according to claim 9, wherein:
the display application of past examination is a display application for a report on the past examination, and
the examination displayed in a display area of the display application for a list of past examination is an examination record.

* * * * *